(12) United States Patent
Lee

(10) Patent No.: US 9,759,677 B2
(45) Date of Patent: Sep. 12, 2017

(54) BIOSENSOR

(71) Applicant: JOINSOON MEDICAL TECHNOLOGY CO., LTD., New Taipei (TW)

(72) Inventor: Jen Fang Lee, New Taipei (TW)

(73) Assignee: Joinsoon Medical Technology Co., Ltd., New Taipei (TW)

( * ) Notice: Subject to any disclaimer, the term of this patent is extended or adjusted under 35 U.S.C. 154(b) by 618 days.

(21) Appl. No.: 13/855,726

(22) Filed: Apr. 3, 2013

(65) Prior Publication Data

US 2013/0256131 A1    Oct. 3, 2013

Related U.S. Application Data

(60) Provisional application No. 61/619,790, filed on Apr. 3, 2012.

(51) Int. Cl.
*G01N 27/327* (2006.01)
(52) U.S. Cl.
CPC .................. *G01N 27/327* (2013.01)

(58) Field of Classification Search
CPC ...... G01N 27/327–27/3274; C12Q 1/00–1/006
See application file for complete search history.

(56) References Cited

U.S. PATENT DOCUMENTS

| 7,138,041 B2* | 11/2006 | Su ....................... G01N 27/3272 204/403.01 |
| 2005/0013731 A1* | 1/2005 | Burke ................. G01N 33/558 422/400 |
| 2006/0278525 A1* | 12/2006 | Petyt .................. G01N 27/3272 204/403.01 |

* cited by examiner

*Primary Examiner* — J. Christopher Ball
(74) *Attorney, Agent, or Firm* — Steven Reiss

(57) ABSTRACT

The present invention disclosed a biosensor apparatus comprising a substrate on which a reaction region is defined, a fluid channel defining a path to the reaction region, and a venting means communicably coupled with the fluid channel and opening exterior of the biosensor apparatus at a perimeter side of the biosensor apparatus. The present invention allows air to exit the fluid channel through perimeter sides of the biosensor apparatus without adding significant manufacturing complexity.

18 Claims, 16 Drawing Sheets

BIOSENSOR

CROSS REFERENCE TO RELATED APPLICATION

This application claims priority to Application Ser. No. 61/619,790 filed on Apr. 3, 2012 which is incorporated by reference in its entirety.

TECHNICAL FIELD

The present disclosure relates to a biosensor apparatus. More particularly, the present disclosure relates to a biosensor apparatus such as a blood glucose test strip that is configured to allow air to exit

BACKGROUND

Aspects of the present invention relate generally to the field of biosensor design, and more specifically to the design of a blood glucose test strip.

In a blood glucose metering system, a conventional test strip typically employs a venting hole on the cover layer of a test strip. For example, as shown in FIG. 1, the test strip consists of a cover layer 100, a spacer 200 and a base layer 300. Typically, the spacer 200 is sandwiched between the cover layer 100 and the base layer 300. Once the spacer 200 is combined with the cover layer 100 and the base layer 300, a channel 210 is formed, and the blood can flow from the opening of the channel 210 to the reaction area. In order to facilitate the blood flow inside the channel 210, the bottom surface of the cover layer would be hydrophilic in order to facilitate capillary motion inside the channel. In addition, to further facilitate the blood flow, the cover layer 100 comprises of a venting hole 110 such that, when the blood enters the channel, air can exit through the venting hole 110.

A problem in regard to the previous configuration is that forming the venting hole 110 on the cover layer 100 limits the strip's design flexibility. Moreover, because the blood may stop flowing once reached the venting hole 110, the venting hole 110 will have to be placed after the reaction zone, thereby further limiting the design flexibility. In addition, the blood may sometimes flow through the venting hole 110, thereby causing possible contamination.

Accordingly, there is a need for a design allowing air to exit the channel through lateral sides of the blood glucose test strip, without adding significant manufacturing complexity.

BRIEF DESCRIPTION OF THE DRAWINGS

The present disclosure is to be read in conjunction with the accompanying drawings, in which.

SUMMARY

Figure 1:
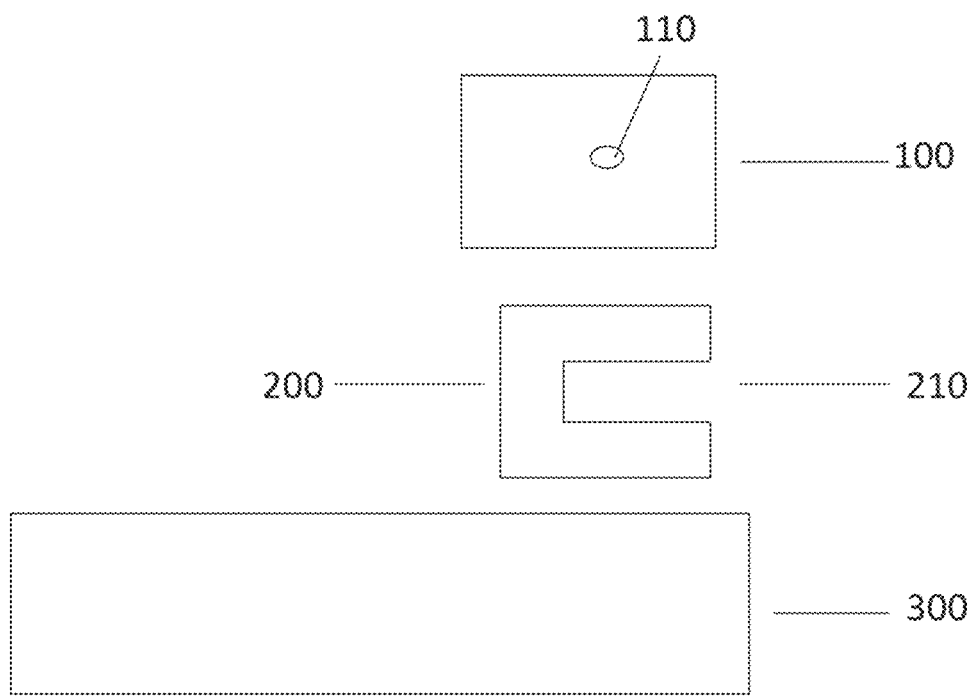
FIG. 1 illustrates a schematic diagram of a conventional biosensor apparatus.

In light of the above, the present disclosure provides a biosensor apparatus to allow air to exit the channel through perimeter sides of a biosensor without adding significant manufacturing complexity.

According to one aspect, a biosensor apparatus comprises a substrate on which a reaction region is defined, a fluid channel defining a path to the reaction region, and a venting means communicably coupled with the fluid channel and opening exterior of the biosensor apparatus at a perimeter side of the biosensor apparatus. The apparatus may further comprise a spacer layer disposed on the substrate to define the fluid channel, and a cover layer disposed on the spacer layer. The cover layer may comprise an optically transparent material and wherein a bottom surface of the cover layer adjacent the fluid channel is hydrophilic. This allows the user to observe and determine the volume of introduced blood.

In one embodiment, the venting means may comprise a passageway disposed on a bottom surface of the cover layer for discharging the air through one or more of lateral sides and back side of the cover layer. Still, the venting means may comprise at least one part of a linear passageway that is substantially perpendicular to the path of the fluid channel. The venting means may otherwise comprise a passageway disposed on an upper surface of the substrate for discharging the air through one or more of lateral sides of the substrate and a back side of the spacer layer opposing an opening of the fluid channel. Still, the venting means may comprise a passageway disposed on the spacer layer and communicably coupled to an end portion of the fluid channel, the passageway capable of discharging the air through one or more sides of the spacer layer.

In one embodiment, the apparatus comprising a dielectric layer disposed on the substrate, the dielectric layer comprising a reaction chamber that defines the reaction region. The venting means in this embodiment may comprise a passageway disposed on a rear portion of the dielectric layer for discharging the air through one or more of lateral sides and a back side of the dielectric layer. The dielectric layer may comprise a stopping chamber communicably coupled between an end portion of the fluid channel and the venting means, wherein the stopping chamber comprises a cross sectional area substantially greater than that of the fluid channel. In another embodiment, the spacer layer may further define a stopping chamber at an end portion of the fluid channel, the stopping chamber having a cross sectional area substantially greater than that of the fluid channel. The stopping chamber may be communicably coupled between the fluid channel and the venting means, wherein the stopping chamber may comprise a cross sectional area substantially greater than that of the fluid channel. This stopping chamber helps slow down the velocity of blood inflow into the fluid channel.

In one embodiment, a top surface, a bottom surface, and said perimeter side define a geometrical dimension of the biosensor apparatus.

In one embodiment, a biosensor apparatus may comprise a substrate on which a reaction region is defined, a fluid channel for introducing a fluid sample to the reaction region, a venting channel communicably coupled with the fluid channel, and a sample reservoir communicably coupled between the fluid channel and the venting channel. In this embodiment, the sample reservoir may comprise a cross sectional area substantially greater than that of the fluidic channel.

In one embodiment, the biosensor apparatus may further comprise a spacer layer disposed on the substrate to define the fluid channel. In another embodiment, the biosensor apparatus may further comprise a cover layer disposed on the spacer layer, wherein the venting channel is disposed on a bottom surface of the cover layer for discharging the air through a perimeter side of the cover layer. In these embodiments, the venting channel may be disposed on a rear portion of the spacer layer for discharging the air through a perimeter side of the space layer. In addition, the venting channel is disposed on an upper surface of the substrate for discharging the air through a perimeter side of the substrate.

In one embodiment, the biosensor may further comprise a dielectric layer disposed between the spacer layer and the substrate, the dielectric layer comprising a reaction chamber that defines the reaction region, and a stopping chamber that defines the sample reservoir. The stopping chamber may comprise a cross sectional area substantially greater than that of the fluid channel. It is to be noted that the description above is only a summary of the invention and a person having ordinary skill in the art would appreciate that the present invention may be applied in a different way other than the disclosed.

DETAILED DESCRIPTION

Embodiments of the present invention provide a blood glucose test strip that employs a capillary channel for the blood flow and at least one venting means to allow air to exit the capillary channel once the blood flows inside. It should be noted that, although the present invention is preferably employed to test glucose level inside a blood sample, a person of ordinary skill in the art would appreciate that the present invention may be applied to all kinds of biological samples (such as blood, urine, and saliva) and may be employed to test one or more biological characteristics within the biological sample. The biological characteristics include, but not limited to, uric acid, cholesterol, hemoglobin, ketone body, glycohemoglobin (HbA1c), and alpha-fetoprotein (AFP).

Figure 2:
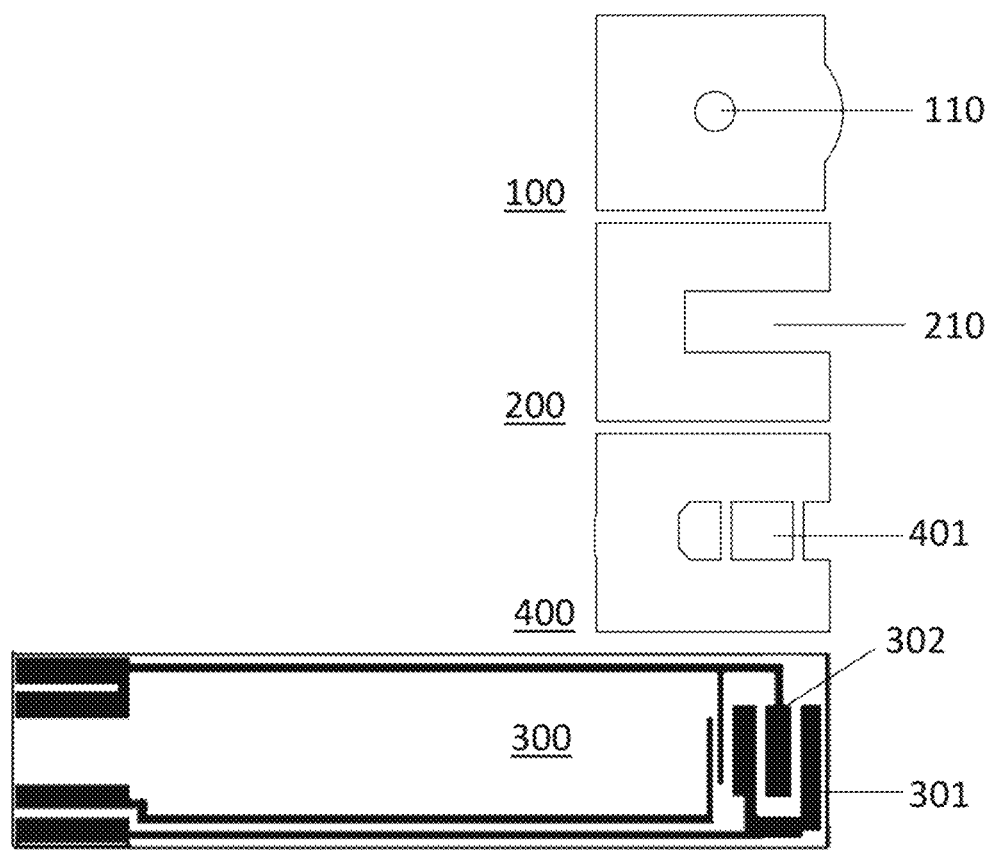
FIG. 2 illustrates a schematic diagram of a biosensor apparatus in accordance with an embodiment of the present disclosure.

As best shown in FIG. 2, the test strip may generally have a layered structure. Working upward from the lowest layer, the test strip may comprise a base layer 300 extending along the entire length of the test strip.

The base layer 300 may preferably consist of an electrically insulating material and may have a thickness sufficient to provide necessary structural support for the test strip. For example, the insulating material for a base layer 300 may be polyester, polytetrafluoroethylene (Teflon), FR-1, CEM-1, CEM-3, FR-2 (Phenolic cotton paper), FR-3 (Cotton paper and epoxy), FR-4 (Woven glass and epoxy), FR-5 (Woven glass and epoxy), FR-6 (Matte glass and polyester), G-10 (Woven glass and epoxy), CEM-1 (Cotton paper and epoxy), CEM-2 (Cotton paper and epoxy), CEM-3 (Non-woven glass and epoxy), CEM-4 (Woven glass and epoxy), CEM-5 (Woven glass and polyester), or any other insulating material that can provide necessary support for the test strip. In addition, the base layer 300 may comprise conductive electrodes, wires, and contact pads, which may be used for testing or for communicating with the test meter. For example, electrodes 301 and 302 may measure the voltage drop or current flow across electrodes 301 and 302. The test meter may contact electrodes 301 and 302 to detect one or more biological characteristics associated with the blood sample in the reaction chamber and may use the other electrodes to check whether a sufficient amount of blood sample has been obtained, or to check whether a test strip has been properly inserted. These conductive electrodes, wires, and contact pads may be made of thin copper foil, gold, or any other non-insulating material.

The next layer in the test strip may be a dielectric layer 400 disposed on the base layer 300. The dielectric layer 400 may cover only part of the base layer 300. In addition, it may include a reaction chamber 401 that is used to deposit the reagent or testing enzyme used to react with the blood sample. A dielectric layer 400 may be made of any insulating material, such as polyester.

The next layer in the test strip may be a channel layer 200. A hollow in a channel layer 200 may form a channel 210 that allows the blood sample to reach the reaction chamber 401. The channel layer 200 may preferably be made of an adhesive material that allows a channel layer 200 to adhere to the dielectric layer 400 and the cover layer 100.

The next layer in the test strip may be a cover layer 100 that is used to form a protective shield for a channel layer 200, and possibly to form the upper boundary of the channel 210. The lower boundary of the channel 210 may be formed by the dielectric layer 400, or by the combination of the dielectric layer 400 and the base layer 300. A cover layer 100 may be made of a transparent material such that the user of the test strip may observe the blood sample in the channel 210, and therefore may determine whether a sufficient amount of blood sample has been provided to the test strip.

As previously mentioned, in order to facilitate the blood flow inside the channel 210, the bottom surface of the cover layer may be hydrophilic to pull the blood sample toward the reaction chamber 401. In addition, the base layer 300 and the dielectric layer 400 may also receive hydrophilic surface treatment to further increase the pulling force applied on the blood sample.

When the blood sample enters the channel 210, the air inside the channel 210 becomes compressed, thereby reducing the blood flow velocity and possibly causing the blood to stop flowing completely. Thus, discharging the air inside the channel 210 is necessary to allow the blood sample to reach the reaction chamber 401 efficiently.

In FIG. 2, the venting hole 110 is formed on the cover layer 100. The venting hole is located above the channel 210, thereby allowing the air to exit through the venting hole 110 when the blood sample enters the channel 210.

Figure 3:
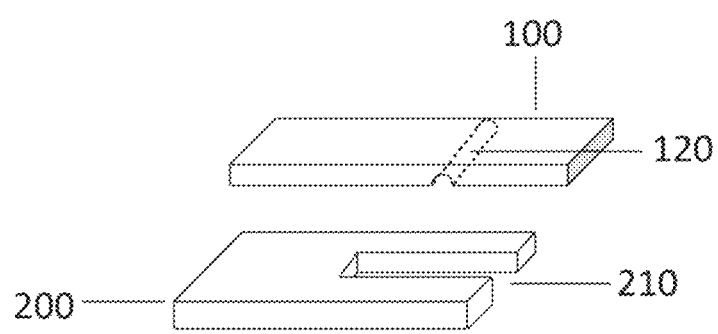
FIG. 3 is a drawing showing a venting means in accordance with an embodiment of the present disclosure.

Alternatively, the venting channel 120 may be formed on the cover layer 100 to allow the air to enter through the venting channel 120 and exit through its opening(s). In the present embodiment, the venting channel 120 is a passageway disposed on a bottom surface of the cover layer 100 for discharging the air through one or more of lateral sides and a back side of the cover layer 100. For example, in FIG. 3, the air inside the channel 210 may be vented through the venting channel 120 and exits through the two openings located on the lateral sides of the cover layer 100.

Figure 4:
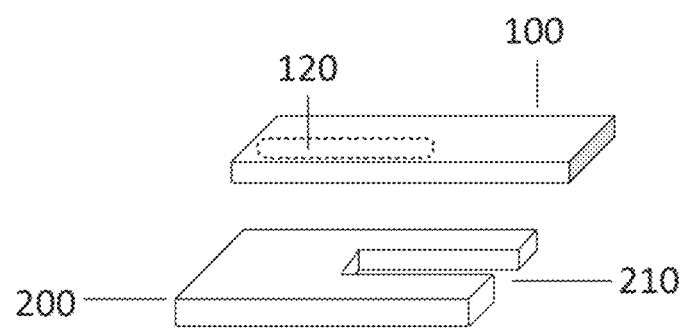
FIG. 4 is a drawing showing a venting means in accordance with an embodiment of the present disclosure.

A person of ordinary skill in the art would appreciate that the direction of the venting channel 210 is not material for the present invention. For example, as shown in FIG. 4, the exit opening of the venting channel 120 may be located at the back side of the cover layer 100.

Figure 5:
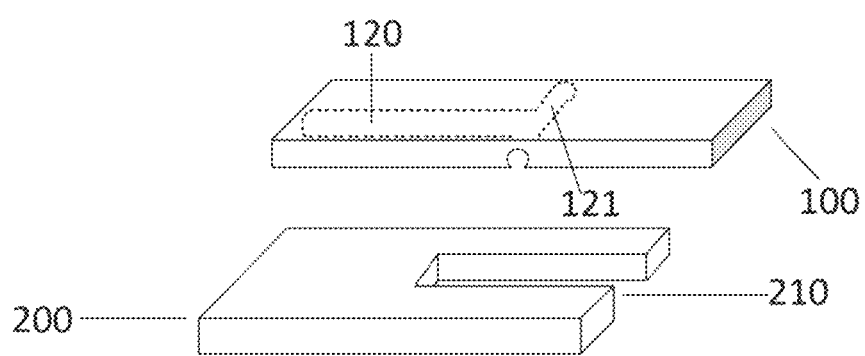
FIG. 5 is a drawing showing a venting means in accordance with an embodiment of the present disclosure.

In addition, a person of ordinary skill in the art would appreciate that the cover layer may comprise multiple venting channels and/or venting holes to discharge the air in the channel 210. For example, in FIG. 5, the cover layer 100 may comprise the venting channel 120 and the venting channel 121. A person of ordinary skill in the art would appreciate that not all venting channels must be overlapped with the channel 210—the air inside the channel 210 may first enter a first venting channel and then redirected or divided into a second venting channel.

Figure 6:
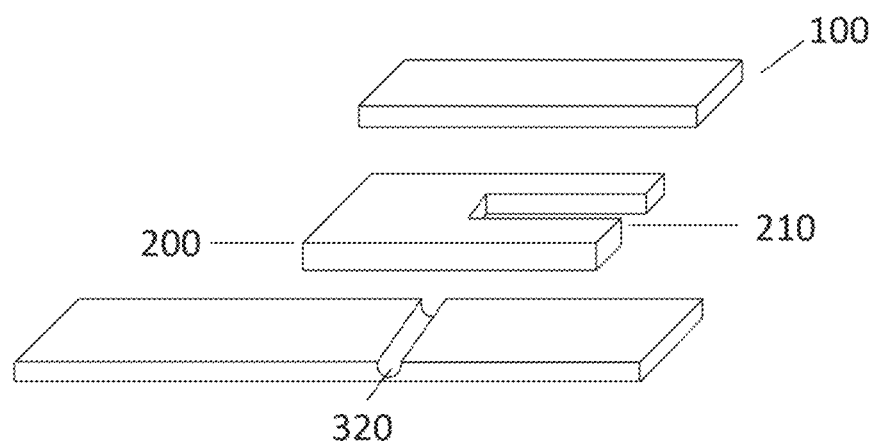
FIG. 6 is a drawing showing a venting means in accordance with an embodiment of the present disclosure.
Figure 7:
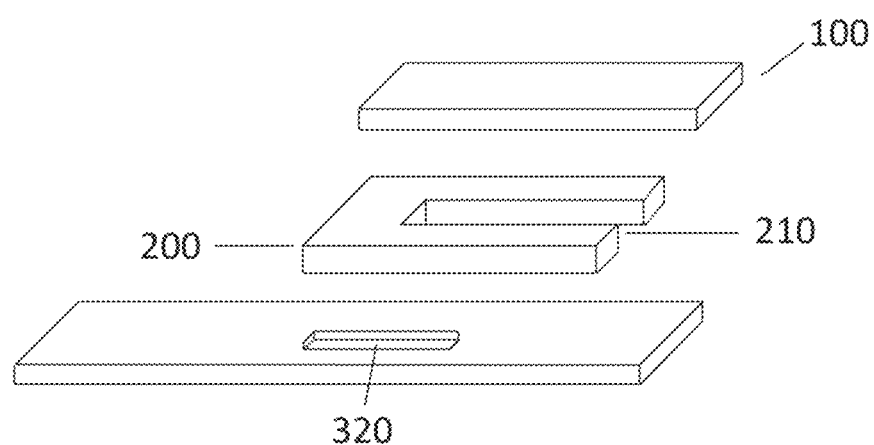
FIG. 7 is a drawing showing a venting means in accordance with an embodiment of the present disclosure.

A person of ordinary skill in the art would appreciate that the similar venting mechanism may also be employed in the base layer. For example, the venting channel may be formed on the base layer 100. As depicted in FIG. 6 (for the sake of clarity, the electrodes, wires, contact pads and dielectric layers are omitted), the venting channel 320 may be formed on the base layer 300 so that the air may exist from venting channel 320 once the blood enters into the channel 210. The direction of the venting channel 320 may be substantially perpendicular to the channel 210, as depicted in FIG. 6, or parallel to the channel 210, as depicted in FIG. 7. In FIG. 6, the venting channel 320 is a passageway disposed on an upper surface of the base layer 100 for discharging the air through one or more of lateral sides of the base layer 100. In FIG. 7, the venting channel 320 is a passageway disposed on an upper surface of the base layer 100 for discharging the air through a back side of the base layer 100 opposing an opening of the channel 210. A person of ordinary skill in the art would appreciate that multiple venting channels and/or venting holes may be formed on the base layer 300 and the directions of the venting channels are not material for the present invention.

Figure 8:
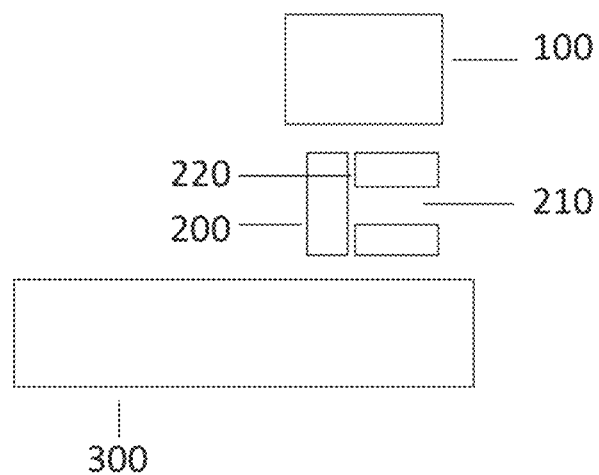
FIG. 8 illustrates a schematic diagram of a biosensor apparatus in accordance with an embodiment of the present disclosure.

Similarly, the venting channel 220 may also be formed on the spacer 200. In the present embodiment, the venting channel 220 is a passageway disposed on the spacer layer 200 and communicably coupled to an end portion of the fluid channel 210, the passageway 221 is capable of discharging the air through one or more sides of the spacer layer 200. As depicted in FIG. 8 (for the sake of clarity, the electrodes, wires, contact pads and dielectric layers are omitted), the venting channel 220 is connected to the channel 210 such that air may exist from the venting channel 220 once it enters into the channel 210.

Figure 9:
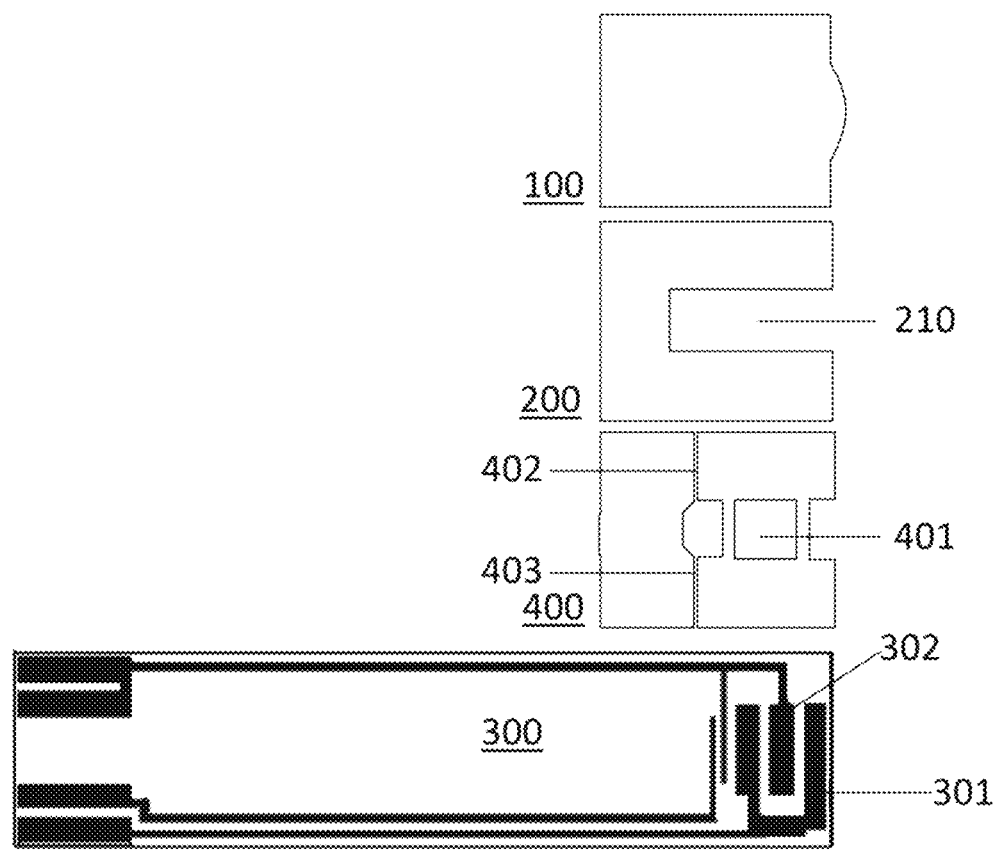
FIG. 9 illustrates a schematic diagram of a biosensor apparatus in accordance with an embodiment of the present disclosure.

In addition to forming the venting channel on the cover layer, on the base layer, or on the dielectric spacer, the venting channel may also be formed on a separate layer that is adjacent to the channel layer. For example, as depicted in FIG. 9, the venting channels 402 and 403 in the dielectric layer 400 may be used to discharge air inside channel 210. In the present embodiment, the venting channel 402 is a passageway disposed on a rear portion of the dielectric layer 400 for discharging the air through one or more of lateral sides of the dielectric layer 400. Thus, when the blood sample enters into the channel 210, air may exit from the venting channels 402 and 403 located in the dielectric layer 400.

Figure 10:
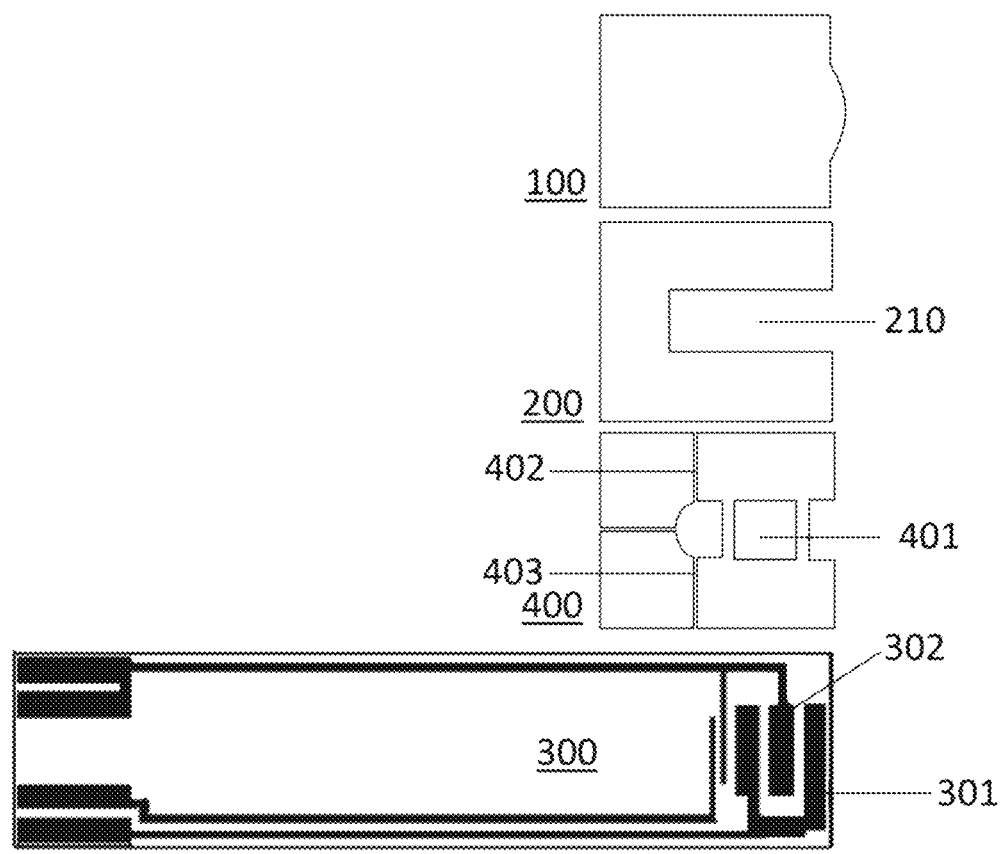
FIG. 10 illustrates a schematic diagram of a biosensor apparatus in accordance with an embodiment of the present disclosure.
Figure 11:
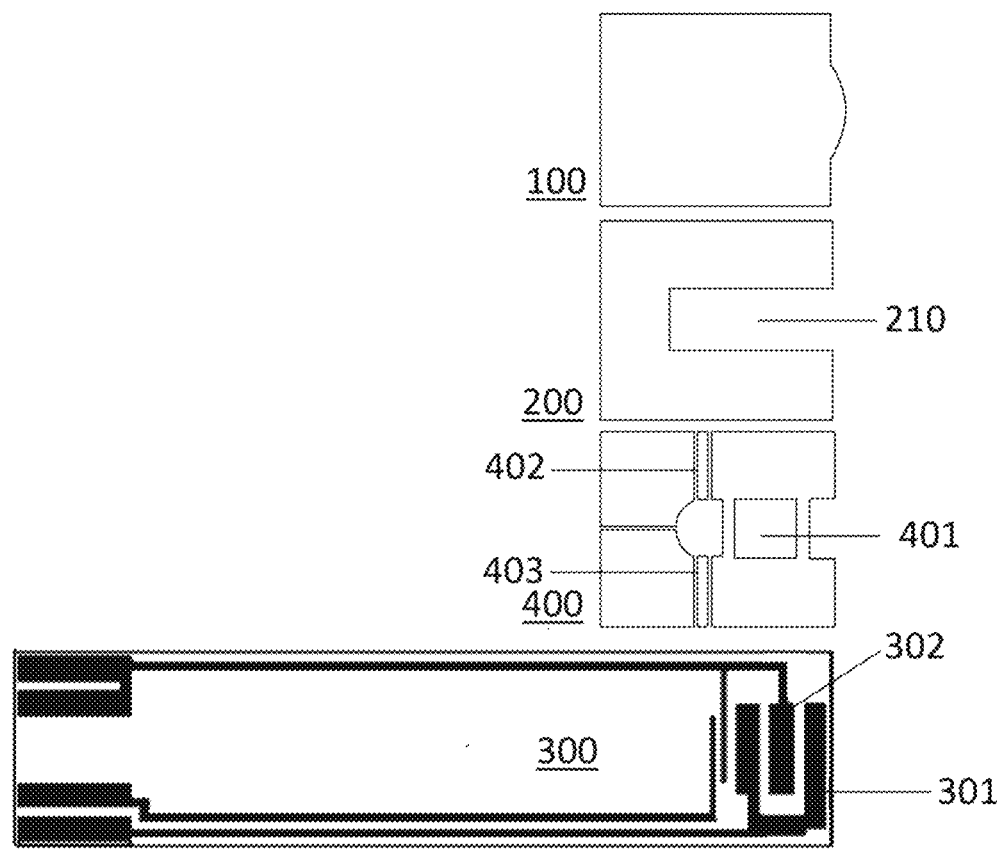
FIG. 11 illustrates a schematic diagram of a biosensor apparatus in accordance with an embodiment of the present disclosure.

The dielectric layer 400 may have multiple venting channels. For example, in FIG. 10, the dielectric layer 400 may have 3 venting channels, two at the lateral sides of the dielectric layer 400 and one at the back of the dielectric layer 400. In the present embodiment, the venting channel 402 is a passageway disposed on a rear portion of the dielectric layer 400 for discharging the air through a back side of the dielectric layer 400. In FIG. 11, the dielectric layer 400 may have 5 venting channels, four at the two lateral sides of the dielectric layer 400 and one at the back side of the dielectric layer 400.

As previously described, the venting channels 210 may be formed on the base layer 300, the dielectric layer 400, the channel layer 200, and the cover layer 100. In addition, the vent openings may be formed on the cover layer 100 and the base layer 300. A person of ordinary skill in the art would appreciate that the principle of the present invention applies to different combinations of the venting mechanisms. For example, the air inside the channel 210 may be vented through both the venting channels in the dielectric layer 400 and the venting channel on the cover layer 100.

Figure 12:
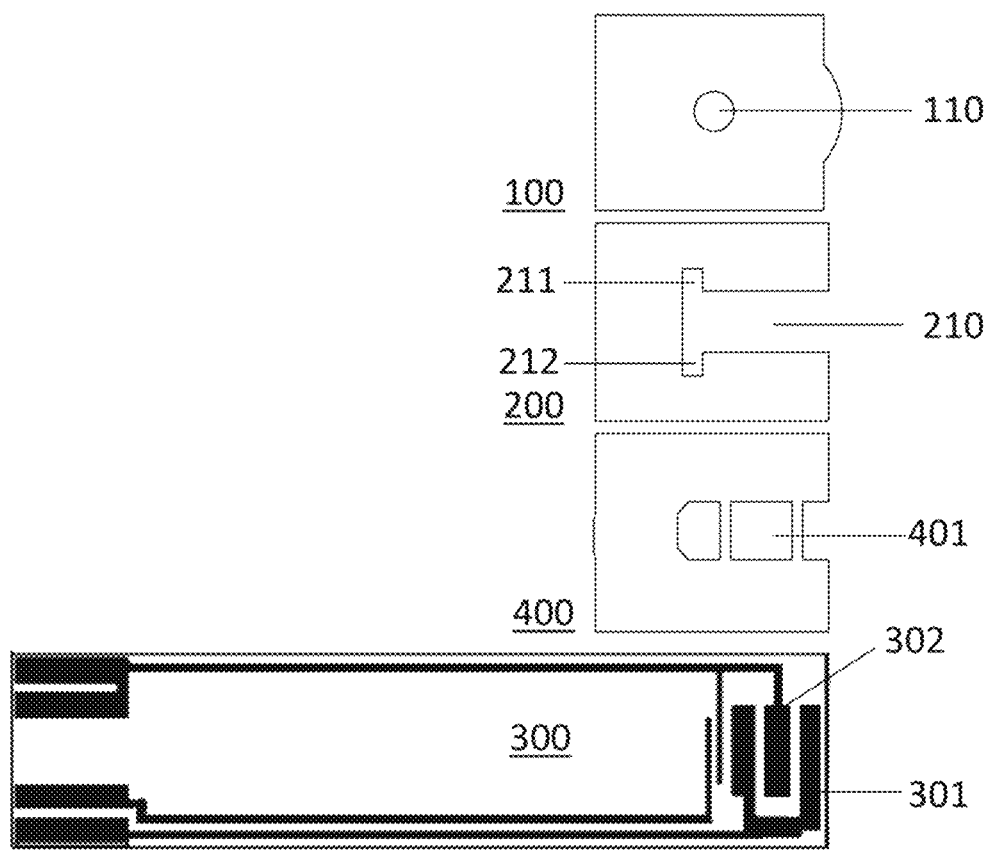
FIG. 12 illustrates a schematic diagram of a biosensor apparatus in accordance with an embodiment of the present disclosure.

FIG. 12 depicts another embodiment of the present invention. As shown, the channel layer 200 comprises of a channel 210 and the blood-stopping chambers 211 and 212. By adding the blood-stopping chambers 211 and 212, when the blood sample flows through the interface between the channel 210 and the blood-stopping chambers 211 and 212, the flow would substantially slow down. Slowing down the blood flow at the interface can prevent the blood sample from flowing into the venting channels or venting holes, thereby prevent possible contamination.

Figure 13A:
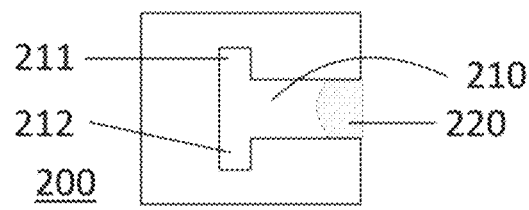
FIGS. 13A, B and C illustrate the process of fluid flow when stopping chambers are employed in accordance with an embodiment of the present disclosure.
Figure 13B:
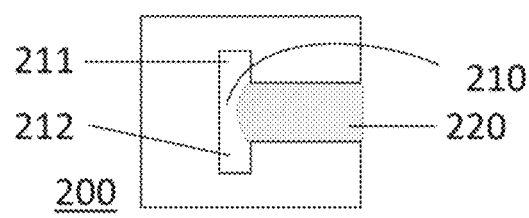
Figure 13C:
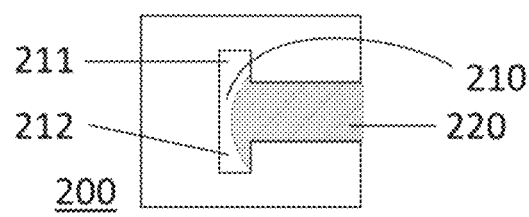

The flow of the blood sample inside the channel layer 200 may be explained in FIGS. 13a, b, and c. In order to maintain an accurate measurement of glucose concentrations, the channel 210 for the sample fluid, whether the blood sample or a control solution, must have a constant cross sectional area, in which the cross sectional area is calculated by multiplying the height of the channel by the width of the channel, for the sample fluid to sip into the channel 210 by capillary force. In FIG. 13a, the blood sample 220 enters into the channel 210. As previously described, the compressed air may exit through the channel through any of the described venting mechanisms. Based on the theory of physics, i.e. continuity equation, in which represents density, V represents flow velocity for fluid and A represents cross sectional area, in a biosensor, the density of the sample fluid does not change over time, and thus the equation becomes $A_1V_1=A_2V_2$. Therefore, if the width of the cross sectional area behind the channel 210 is smaller than that of the channel 210, the flow velocity for the fluid to travel behind the channel 210 will be faster than that in the channel 210, for the same volume of fluid to travel. On the contrary, if the width of the cross sectional area behind the channel 210 is larger than that of the channel 210, the flow velocity for the fluid to travel behind the channel 210 will be slower than that in the channel 210. In the event that if the width of the cross sectional area behind the channel 210 is much larger than that of the channel 210, the flow velocity for the fluid to travel behind the channel 210 will be much slower than that in the channel 210. In FIG. 13b, the blood sample 220 reaches the interface between the channel 210 and the blood-stopping chambers 211 and 212. At this point in time, the blood sample flow would be slowed down once it begins to enter the blood-stopping chambers 211 and 212. In FIG. 14c, the blood sample reaches the blood-stopping chambers 211 and 212 and its flow velocity is substantially lowered.

Figure 14A:
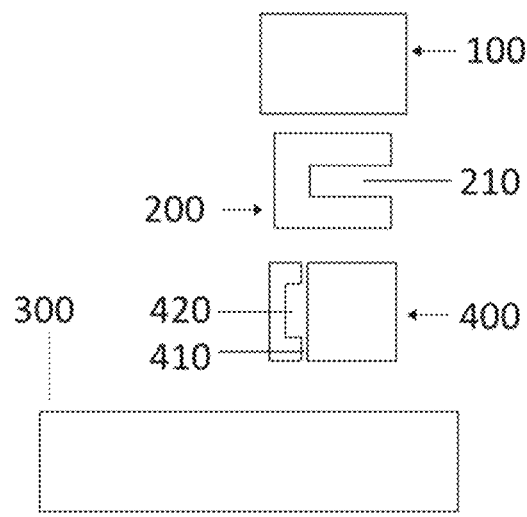
FIGS. 14A and B illustrate schematic diagrams of biosensor apparatus in accordance with an embodiment of the present disclosure.
Figure 14B:
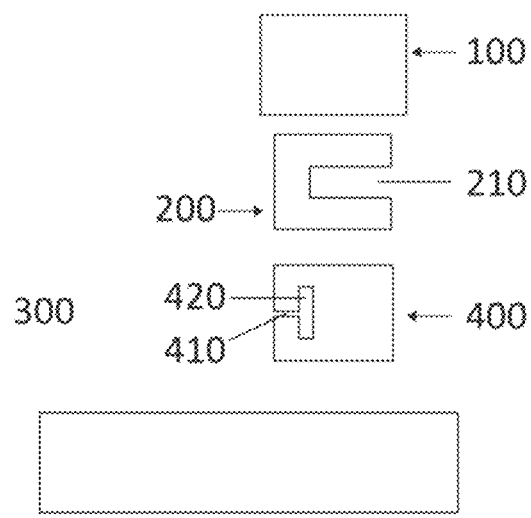

FIGS. 14 a and b depict embodiments of the present invention. In FIGS. 14a and b, the blood sample flow may be slowed down by the abrupt increase in the available flow space caused by the chamber 420 in the dielectric layer 400. In FIG. 14a, the air may exit through the lateral venting channel 410. In FIG. 14b, the air may exit through the back venting channel 410.

Figure 15:
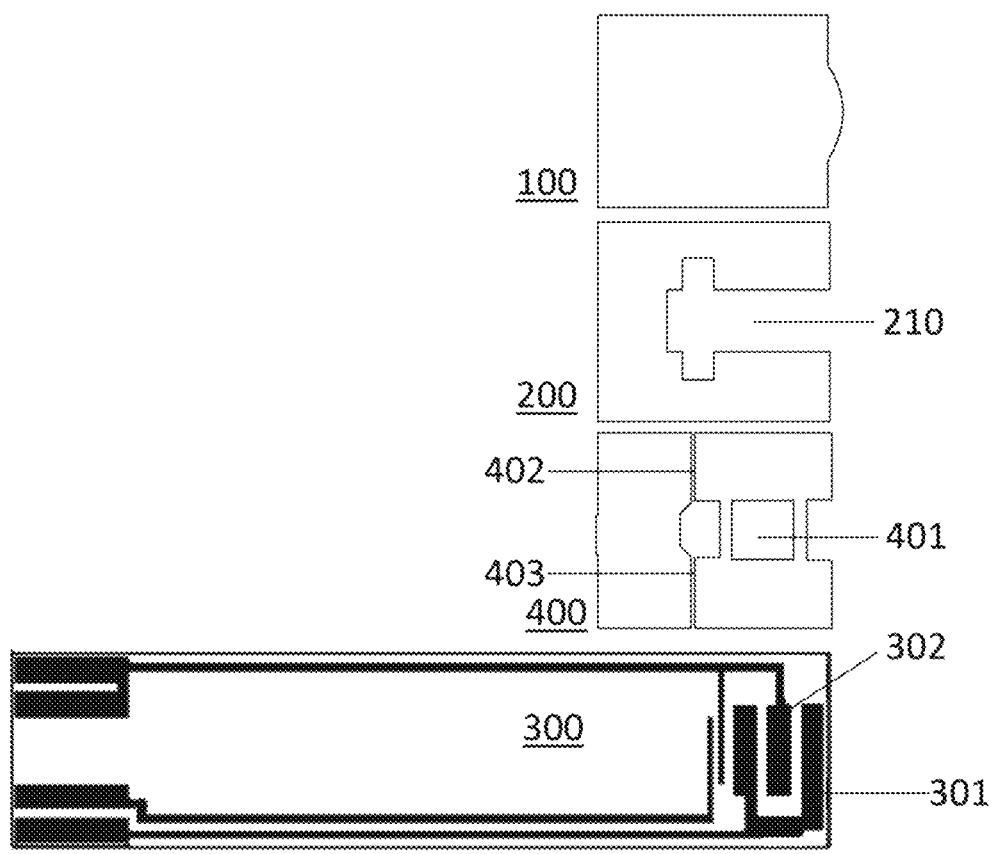
FIG. 15 illustrates a schematic diagram of a biosensor apparatus in accordance with an embodiment of the present disclosure.

FIG. 15 depicts an embodiment of the present invention. As shown, the channel layer 200 has incorporated the blood-stopping chambers previously described to slow down the blood flow. The dielectric layer 400 has incorporated the venting channels 402 and 403. Thus, when the blood sample enters into the channel 210, the air inside the channel may exit through the venting channels 402 and 403. In addition, once the blood sample reaches the blood-stopping chambers in the channel layer 200, the flow of the blood sample would be substantially slowed down.

Figure 16:
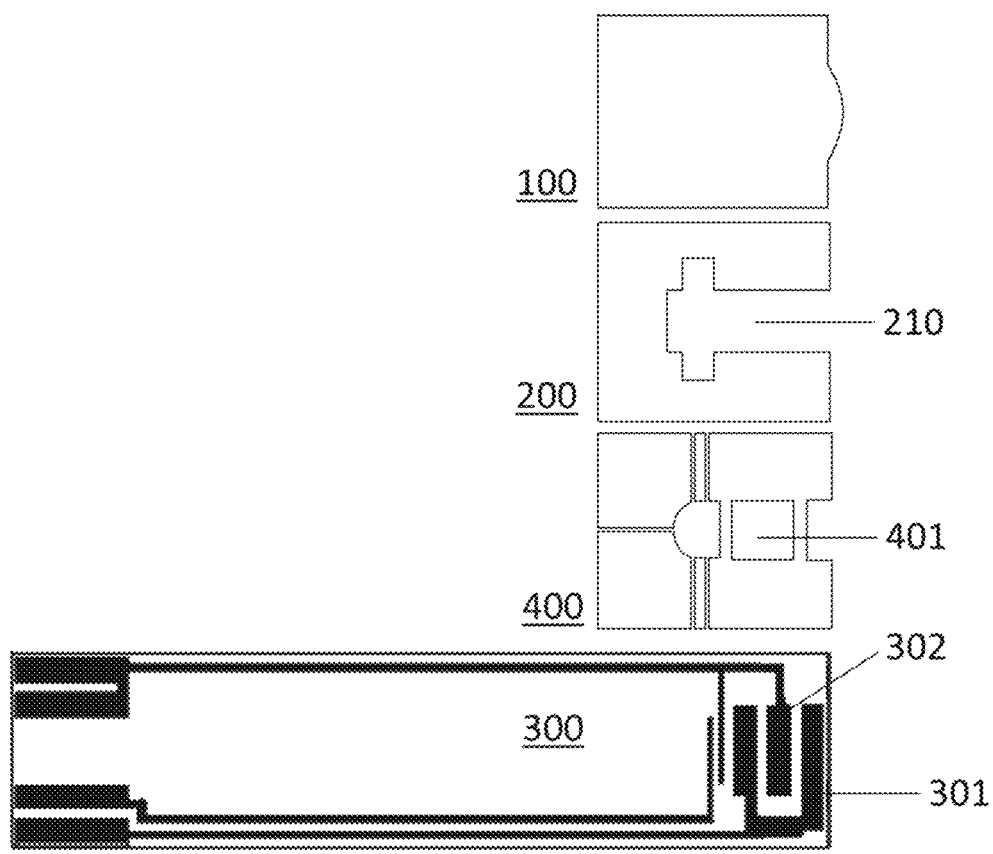
FIG. 16 illustrates a schematic diagram of a biosensor apparatus in accordance with an embodiment of the present disclosure.

A person of ordinary skill in the art would appreciate that the previously described venting mechanisms may be combined with the different types of the blood-stopping mechanisms previously described. For example, in FIG. 16, the blood-stopping mechanism on the channel layer 200 may be combined with the 5 venting channels in the dielectric layer 400.

What is claimed is:

1. A biosensor apparatus comprising:
a substrate on which a reaction region is defined;
a fluid channel defining a path to the reaction region; and
a venting means communicably coupled with the fluid channel and opening exterior of the biosensor apparatus at a perimeter side of the biosensor apparatus, and the venting means comprising a first passageway formed in an upper surface of the substrate for discharging the air through one or more of lateral sides of the substrate.

2. The apparatus of claim 1, wherein at least one part of the first passageway is linear and substantially perpendicular to the path of the fluid channel.

3. The apparatus of claim 1, further comprising a spacer layer disposed on the substrate to define the fluid channel, and a cover layer disposed on the spacer layer.

4. The apparatus of claim 3, wherein the cover layer comprises an optically transparent material and wherein a bottom surface of the cover layer adjacent the fluid channel is hydrophilic.

5. The apparatus of claim 3, wherein the venting means further comprises a second passageway disposed on a bottom surface of the cover layer for discharging the air through one or more of lateral sides and a back side of the cover layer.

6. The apparatus of claim 5, wherein the venting means further comprises a third passageway disposed on the upper surface of the substrate for discharging the air through a back side of the spacer layer opposing an opening of the fluid channel.

7. The apparatus of claim 6, wherein the venting means further comprises a fourth passageway disposed on the spacer layer and communicably coupled to an end portion of the fluid channel, the fourth passageway capable of discharging the air through one or more sides of the spacer layer.

8. The apparatus of claim 3, wherein the spacer layer further defines a stopping chamber at an end portion of the fluid channel, the stopping chamber having a cross sectional area substantially greater than that of the fluid channel.

9. The apparatus of claim 1, further comprising a stopping chamber communicably coupled between the fluid channel and the venting means, wherein the stopping chamber comprises a cross sectional area substantially greater than that of the fluid channel.

10. The apparatus of claim 1, wherein a top surface, a bottom surface, and said perimeter side define a geometrical dimension of the biosensor apparatus.

11. A biosensor apparatus comprising:
a substrate on which a reaction region is defined;
a fluid channel defining a path to the reaction region; and
a venting means communicably coupled with the fluid channel and opening exterior of the biosensor apparatus at a perimeter side of the biosensor apparatus, and
a dielectric layer disposed on the substrate, the dielectric layer comprising a reaction chamber that defines the reaction region, and the venting means comprising a first passageway disposed on a rear portion of the dielectric layer for discharging the air through one or more of lateral sides of the dielectric layer, and a second passageway disposed on the rear portion of the dielectric layer for discharging the air through a back side of the dielectric layer.

12. The apparatus of claim 11, wherein the dielectric layer comprises a stopping chamber communicably coupled between an end portion of the fluid channel and the venting means, wherein the stopping chamber comprises a cross sectional area substantially greater than that of the fluid channel.

13. A biosensor apparatus comprising:
a substrate on which a reaction region is defined;
a fluid channel for introducing a fluid sample to the reaction region;
a venting channel communicably coupled with the fluid channel, and formed in an upper surface of the substrate for discharging the air through a perimeter side of the substrate; and
a sample reservoir communicably coupled between the fluid channel and the venting channel, and the sample reservoir comprising a cross sectional area substantially greater than that of the fluidic channel.

14. The apparatus of claim 13, further comprising a spacer layer disposed on the substrate to define the fluid channel.

15. The apparatus of claim 14, further comprising a cover layer disposed on the spacer layer, wherein the venting channel is disposed on a bottom surface of the cover layer for discharging the air through a perimeter side of the cover layer.

16. The apparatus of claim 14, wherein the venting channel is disposed on a rear portion of the spacer layer for discharging the air through a perimeter side of the space layer.

17. The apparatus of claim 14, further comprising a dielectric layer disposed between the spacer layer and the substrate, the dielectric layer comprising a reaction chamber that defines the reaction region, and a stopping chamber that defines the sample reservoir.

18. The apparatus of claim 17, wherein the stopping chamber comprises a cross sectional area substantially greater than that of the fluid channel.

* * * * *